(12) United States Patent
Wang et al.

(10) Patent No.: US 7,473,239 B2
(45) Date of Patent: Jan. 6, 2009

(54) SINGLE EXPANDABLE DOUBLE LUMEN CANNULA ASSEMBLY FOR VENO-VENOUS ECMO

(75) Inventors: Dongfang Wang, League City, TX (US); Joseph B. Zwischenberger, Galveston, TX (US)

(73) Assignee: The University of Texas System, Austin, TX (US)

( * ) Notice: Subject to any disclaimer, the term of this patent is extended or adjusted under 35 U.S.C. 154(b) by 440 days.

(21) Appl. No.: 10/924,150

(22) Filed: Aug. 23, 2004

(65) Prior Publication Data

US 2005/0085761 A1  Apr. 21, 2005

Related U.S. Application Data

(60) Provisional application No. 60/497,533, filed on Aug. 25, 2003.

(51) Int. Cl.
*A61M 37/00* (2006.01)
*A61M 31/00* (2006.01)

(52) U.S. Cl. ............... 604/6.16; 604/4.01; 604/6.11; 604/508; 604/510

(58) Field of Classification Search ........... 604/4.01, 604/5.01, 6.09, 6.14, 6.16, 93.01, 43, 96.01, 604/103.07, 523, 530–532, 510, 164.13, 604/507, 508; 422/44–48
See application file for complete search history.

(56) References Cited

U.S. PATENT DOCUMENTS

| | | | | |
|---|---|---|---|---|
| 4,406,656 A | * | 9/1983 | Hattler et al. ........... 604/523 |
| 4,738,666 A | * | 4/1988 | Fuqua ................... 604/514 |
| 5,009,636 A | * | 4/1991 | Wortley et al. ........... 604/43 |
| 5,413,557 A | * | 5/1995 | Solar ................. 604/103.1 |
| 5,464,398 A | * | 11/1995 | Haindl ................. 604/523 |
| 5,618,267 A | * | 4/1997 | Palestrant ............. 604/510 |
| 5,858,009 A | * | 1/1999 | Jonkman ............... 604/264 |
| 5,868,717 A | * | 2/1999 | Prosl .................. 604/264 |
| 5,916,193 A | * | 6/1999 | Stevens et al. .......... 604/509 |
| 6,238,409 B1 | * | 5/2001 | Hojeibane .............. 606/194 |

OTHER PUBLICATIONS

Okamoto, T. et al., "Preliminary Experiment with a Newly Developed Double Balloon, Double Lumen Catheter for Extracorporeal Life Support Vascular Access," ASAIO Journal, Sep.-Oct. 2003, pp. 583-588, Department of Anesthesiology, Kumamoto University School of Medicine, Kumamoto, Japan.

(Continued)

*Primary Examiner*—Leslie R Deak
(74) *Attorney, Agent, or Firm*—Locke Lord Bissell & Liddell LLP (57) ABSTRACT

The present invention provides an apparatus, system, and method of use of a simple, less invasive, self-expandable percutaneous double lumen cannula assembly for VV ECMO that overcomes the limitations and obstacles of the techniques described above. The present invention achieves near theoretical total venous blood drainage, total extracorporeal gas exchange, and prevents recirculation and multiple cannulation, thereby simplifying VV ECMO, decreasing surgical and blood trauma, and expanding its application.

49 Claims, 9 Drawing Sheets

OTHER PUBLICATIONS

Ichiba, S. et al., "Modifying a Venovenous Extracorporeal Membrane Oxygenation Circuit to Reduce Recirculation," The Society for Thoracic Surgeons, 2000, pp. 298-299, Elsevier Science Inc. United Kingdom.

Otsu, T. et al., "Laboratory Evaluation of a Double Lumen Catheter for Venovenous Neonatal ECMO," Trans.Am.Artif.Intern Organs, 1989, pp. 647-649, vol. XXXV, University of Michigan Medical School, Department of Surgery, Ann Arbor, Michigan, USA.

Delius, R. et al., "Venovenous compares favorably with venoarterial access for extracorporeal membrane oxygenation in neonatal respiratory failure," 72nd Annual Meeting of The American Association for Thoracic Surgergy. Apr. 1993, pp. 329-338, Mosby-Year Book Inc., USA.

Peek, G.J., et al., "Vascular Access for Extracorporeal Organ Support," ECMO-Extracorporeal Cardiopulmonary Support in Critical Care, 2000, pp. 253-268,, Extracorporeal Life Support Organization, USA.

Anderson, H.L. III, et al., "Multicenter Comparison of Conventional Venoarterial Access Versus Venovenous Double-Lumen Catheter Access in Newborn Infants Undergoing Extracorporeal Membrane Oxygenation," 23rd Annual Meeting of the American Pediatric Surgical Association, May 1992, pp. 630-635, W.B. Saunders Company, USA.

\* cited by examiner

SINGLE EXPANDABLE DOUBLE LUMEN CANNULA ASSEMBLY FOR VENO-VENOUS ECMO

This application claims the benefit of U.S. Provisional Application Ser. No. 60/497,533, filed Aug. 25, 2003.

FIELD OF THE INVENTION

The invention relates to the field of medical devices. More specifically, the invention relates to the design and use of percutaneous medical devices.

BACKGROUND OF THE INVENTION

Although cutting edge critical care technology has been applied in the treatment of Acute Respiratory Distress Syndrome (ARDS), mortality remains at 40%. In theory, ECMO (Extracorporeal Membrane Oxygenation) of blood is continuously an aggressive yet effective treatment for ARDS. The key is obtaining an effective ECMO.

Figure 1:
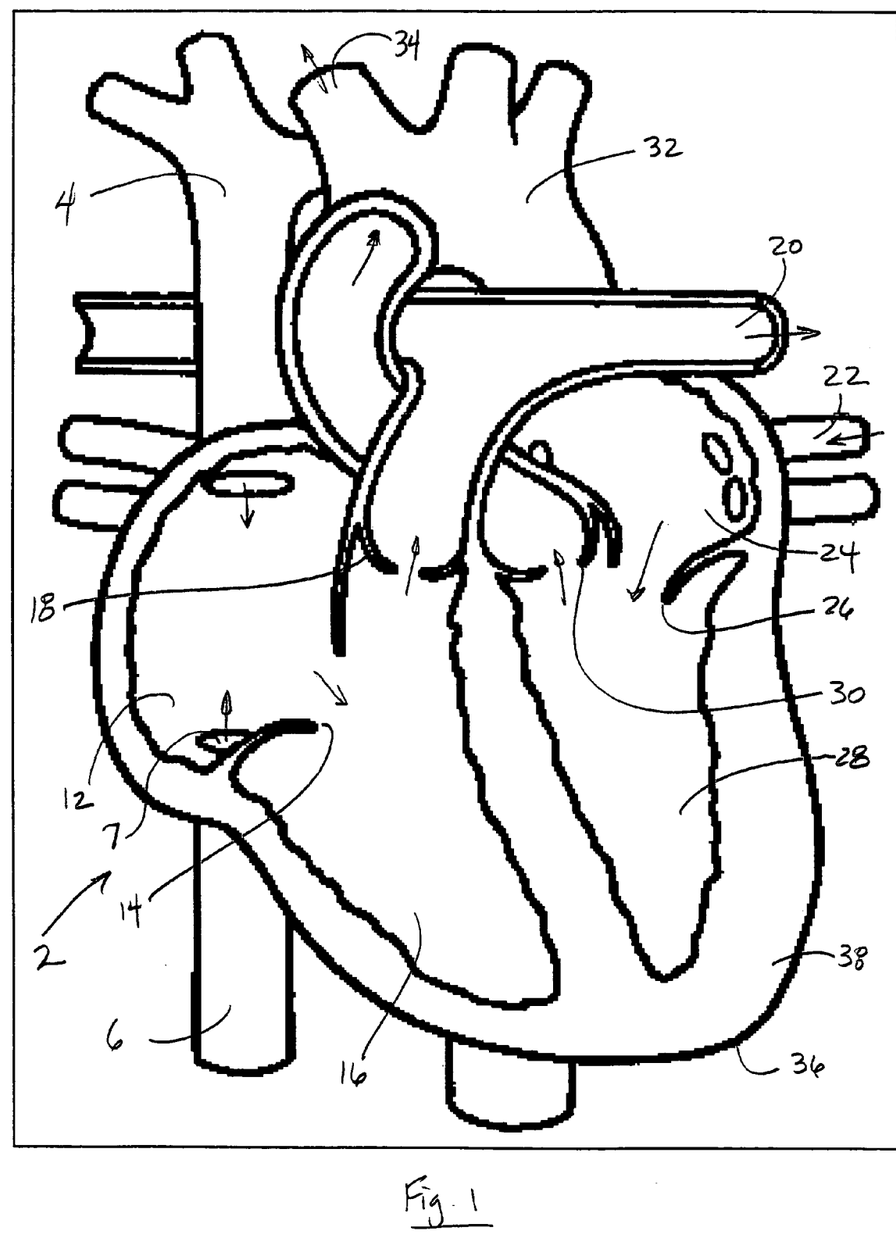
FIG. 1 is a diagram of a heart showing the various portions relevant to the present invention.

FIG. 1 is a diagram of a heart showing various portions for background purposes. The following brief summary of the heart's circulatory system is included to provide a better understanding of ECMO, and the present invention in particular. The heart 2 receives blood from the upper part of the body through the superior vena cava (SVC) 4 and from the lower part of the body through the larger inferior vena cava (IVC) 6 into the right atrium 12 of the heart. A one-way valve of the IVC 7, known as an Eustachian valve, resists blood flow back into the IVC from the right atrium.

The right atrium 12 then contracts to force the blood through the tricuspid valve 14 into the right ventricle 16. The right ventricle 16 contracts at a relatively small contraction pressure to force the blood through the pulmonary valve 18 into the pulmonary artery 20. The pulmonary artery 20 directs blood to the lungs (not shown) where the blood is oxygenated. From the lungs, the oxygenated blood is returned to the heart 2 through pulmonary vein 22 into the right atrium 24. The right atrium 24, again operating a low pressure, such as less than 18 mm of mercury, pushes the blood through the mitral valve 26 into the left ventricle 28. The left ventricle 28 provides the main pumping chamber for the heart at a higher pressure of approximately 100 mm of mercury. The blood pumped from the left ventricle exits through the aortic valve 30 into the aorta 32 in the lower region known as the aortic root. The aorta 32 then acts as a distribution chamber for the various greater arteries 34.

When the lungs are improperly functioning or not functioning at all, the blood flow through the pulmonary circuit results in poorly oxygenated blood. Oxygenation through ECMO can be necessary. However, proper cannulation is critical for ECMO and the key to its effectiveness and heretofore limitations.

ECMO is divided into two major categories according the cannulation and configuration: Veno-Arterial (VA) ECMO and Veno-venous (VV) ECMO. VA ECMO is more popular because of its effective extracorporeal oxygenation. A drainage cannula is introduced into the superior vena cava and an infusion cannula is introduced into the aorta. Blood is drained through the cannula to a pump, the pump circulates the blood through an oxygenator, and the oxygenated blood is returned to the body through an infusion cannula into the aorta. VA ECMO allows an efficient transfer of oxygen into relatively deoxygenated blood from a vein directly to an artery. However, VA ECMO, which cannulates major arteries, is inherently problematic. Traumatic cannulation of major arteries may lead to ligation and/or occlusion of the major arteries (carotid and femoral arteries), massive arterial bleeding, stroke, or amputation. These inherent risks through cannulation of arteries inhibit the widespread use of VA ECMO. Furthermore, VA ECMO circulates oxygenated blood without passing through the heart. Thus, unsaturated or even deoxygenated blood from the dysfunctional native lungs perfuse the heart myocardium and leads to cardiac stun syndrome.

The primary advantage of VV ECMO over VA ECMO is avoidance of major arterial cannulation and the attendant complications described above. Cannulation of veins for the drainage and infusion avoids the higher pressures and problems of cannulating arteries.

The advantage of avoiding arterial cannulation by VV ECMO has been known, but the technology for implementing a practical VV ECMO has eluded researchers and practitioners. The major disadvantages of VV ECMO include (i) multiple venous cannulation which results in further trauma to the patient, (ii) insufficient venous blood drainage caused by limitations on the drainage cannula placement, and (iii) insufficient extracorporeal gas exchange from undesirable blood recirculation by short circuiting of the blood flow path through the body of oxygenated blood mixed with deoxygenated blood, also due to the limitations on the drainage cannula placement.

There are four types of cannula/cannulation in VV ECMO practice: two site, single lumen cannulation VV ECMO; a single double lumen cannulation (DLVV ECMO); a single cannula tidal flow ECMO; and VVV three cannulation ECMO. All of these types of VV ECMO have the problem of either multi-cannulation and/or blood recirculation.

Two site, single lumen ECMO needs multiple cannulations, one for venous blood drainage and the other for oxygenated blood infusion. The drainage cannula is usually inserted from the jugular vein and lays in the SVC. This procedure is unable to drain more than about half (50%) of the venous blood returning to the heart, because it accesses only the SVC and excludes the IVC. Such a low percentage is generally unable to sustain life. The drainage cannula can be slightly further extended through the SVC into the right atrium to drain more than 50% of the venous blood, because both the SVC and IVC discharge into the atrium. However, that extension increases undesirable recirculation of oxygenated blood as the extracorporeal oxygenated blood is returned into the same location, that is, the right atrium. Recirculation of extracorporeal oxygenated blood compromises extracorporeal gas exchange and increases the possibility of blood trauma. Blood trauma includes undesirable hemolysis, activation of inflammatory processes, or coagulinopathies.

Current double lumen, single cannula for VV ECMO is placed via the jugular vein into the SVC. For the same reason as above, maximum extracorporeal venous drainage is also 50% by discharging the blood primarily from the SVC. The remaining 50% of venous return from the IVC is largely not drained for extracorporeal oxygenation due to the placement of the double lumen single cannula. The existence of only a pediatric system, to the knowledge of the inventors, for this type of VV ECMO is evidence of the fact that the above system is only a partial and unsatisfactory solution. An adult version is simply not available that can drain a sufficient supply of venous blood, oxygenate the blood, and return the blood to the atrium at the flow rates needed for adult ECMO of this type. The blood from IVC can be accessed by further advancement of the cannula into the right atrium to allow some additional blood from the IVC to be drained. However, the extension currently results in significant undesirable recirculation of the blood from and into the atrium, and the resulting undesirable blood trauma described above.

The single lumen cannula tidal flow (VV ECMO) avoids multiple cannulation, but requires a more complicated circuit together with a control system. This type is essentially a batch ECMO, where a quantity of blood is withdrawn from the body through a single lumen, oxygenated external to the body, then returned through the same lumen to the same location in the body. This technology cannot eliminate the recirculation because the drainage and infusion locations are the same. The quantity needs to be small enough to not disturb the hemodynamic flow and yet large enough to provide a substantial amount of oxygenation to the body. High flow blood back and forward in the cannula causes blood trauma, described above.

Recently, three individual venous cannulations (the right jugular vein, and left and right femoral veins) have been reported to achieve near total venous blood drainage without increasing undesirable recirculation (Ichiba, S. et al: *Modifying Venous Extracorporeal Membrane Oxygenation Circuit to Reduce Recirculation*, Ann Thorac Surg, 2000; 69:298-9). However, the procedure uses three traumatic large venous cannulations and a large extracorporeal volume with long, complicated tubing circuit. Thus, the flow rate and oxygenation is increased, but the trauma to the patient can prevent its wide acceptance for effective VV ECMO.

Therefore, there remains a need for a simple, less invasive, percutaneous cannula system and method.

SUMMARY OF THE INVENTION

The present invention provides an apparatus, system, and method of use of a simple, less invasive, self-expandable percutaneous double lumen cannula, in at least one embodiment, for VV ECMO that overcomes the limitations and obstacles of the techniques described above. The present invention can achieve near theoretical total venous blood drainage, extracorporeal gas exchange. It reduces recirculation and multiple cannulation, thereby simplifying VV ECMO, resulting in decreased surgical and blood trauma for the patient.

The invention provides a system for mixing a fluid into a bloodstream of a body, comprising: a drainage cannula adapted to be inserted through both a superior vena cava of a heart of the body and an inferior vena cava of the heart, the drainage cannula having an opening to receive blood from a superior vena cava blood flow and separate opening to receive blood from an inferior vena cava blood flow; an infusion cannula adapted to be inserted into the bloodstream downstream of both the superior vena cava and inferior vena cava; a pump coupled to the drainage cannula and the infusion cannula; and a mixing unit coupled to the pump and adapted to mix the fluid into the bloodstream of the body.

The invention also provides a system for mixing a fluid into a bloodstream of a body, comprising: a drainage means for draining blood from both a superior vena cava of a heart of the body and an inferior vena cava of the heart; an infusion means for infusing the fluid into the bloodstream downstream of both the superior vena cava and inferior vena cava; a pump coupled to the drainage means and the infusion means; and a mixing unit coupled to the pump and adapted to mix the fluid into the bloodstream of the body.

The invention further provides a method of perfusing a fluid into a bloodstream of a body, comprising: draining blood through a common drainage cannula from a superior vena cava of a heart of the body and an inferior vena cava of the heart; pumping the blood through a mixing unit to combine a fluid with the blood; and infusing the fluid with the blood into the body through an infusion cannula.

The invention includes a cannula assembly for draining and infusing blood in a body, comprising: an elongated first portion forming a first lumen and a longitudinal slot formed in a sidewall of the first portion, the slot having a first side and a second side; and a flexible member sealingly coupled to the first portion on both sides of the slot to cover the longitudinal slot in an expanded state of the cannula.

Further, invention includes a cannula assembly for draining and infusing blood in a body, comprising: an elongated first portion forming a first lumen; and an elongated second portion coupled to the first portion forming a second lumen.

BRIEF DESCRIPTION OF THE DRAWINGS

A more particular description of the invention, briefly summarized above, may be had by reference to the embodiments thereof which are illustrated in the appended drawings and described herein. It is to be noted, however, that the appended drawings illustrate only some embodiments of the invention and are therefore not to be considered limiting of its scope, because the invention may admit to other equally effective embodiments.

DETAILED DESCRIPTION OF A PREFERRED EMBODIMENT

Figure 2:
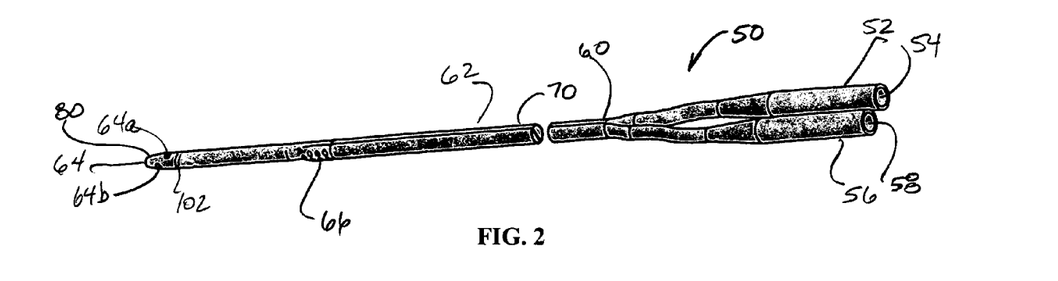
FIG. 2 is a perspective schematic view of one embodiment of a cannula assembly of the present invention.
Figure 2A:
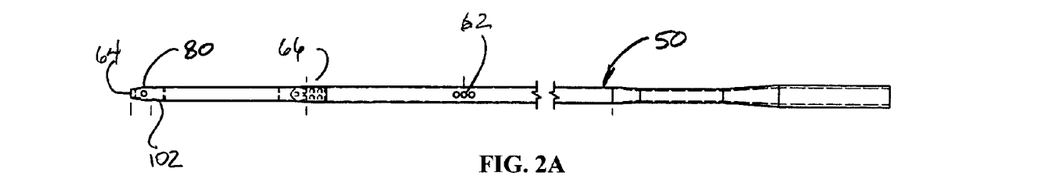
FIG. 2A is a side view of the cannula assembly of FIG. 2.
Figure 2B:
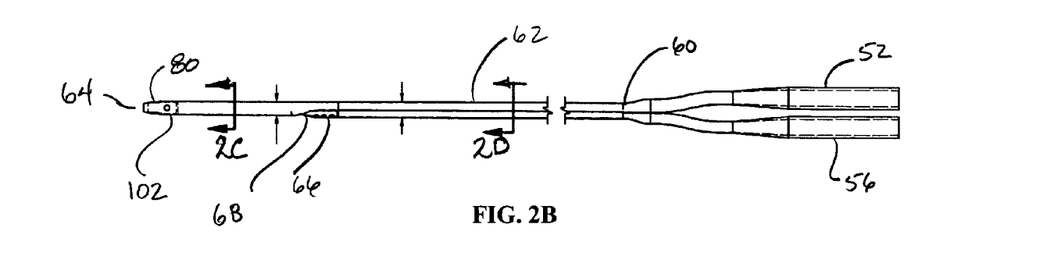
FIG. 2B is a top view of the cannula assembly of FIG. 2.

FIG. 2 is a perspective schematic view of a cannula assembly of the present invention. FIG. 2A is a side view of the cannula assembly of FIG. 2. FIG. 2B is a top view of the cannula assembly of FIG. 2. The figures will be described in conjunction with each other and similar components are labeled similarly throughout.

A cannula assembly 50 generally includes a drainage cannula 52 and an infusion cannula 56. A drainage cannula 52 forms a first lumen 54 and the infusion cannula 56 forms a second lumen 58. In at least one embodiment each of the cannulae has a sidewall which when it merges into a single cannula assembly becomes a sidewall of the cannula assembly. The cannula are illustrated as separate components toward an upper end of the cannula assembly as could be advantageous for conventional coupling to tubing and other instruments in the medical field; however, it is understood that such a separation is not necessarily in the invention. In the illustrated embodiment, the cannulae converge in a first transition zone 60 into a cannula assembly having two lumen. One lumen functions as the drainage cannula and the second lumen functions as the infusion cannula.

A first opening 62 is disposed along the length of one lumen, such as the drainage lumen. The opening 62 can include several small openings or a single larger opening as may be appropriate to the particular process. A second opening 64 is formed generally in the same lumen as the opening 62. The opening 64 can include an end opening, or side openings 64A, 64B, collectively referred to herein as the opening 64. In general, the opening 62 and the opening 64 will be formed in the drainage cannula 52 and thus be fluidicly coupled to each other. A third opening 66 is formed in the other cannula, for example, the infusion cannula. The opening 66 is generally sealed from the openings 62, 64 and has a different flow path.

In the illustrated embodiment, blood will be drained. The openings 62, 64 in the drainage cannula 52 will drain the blood from the body and allow processing, described below. The infusion cannula 56 through the infusion lumen 58 will return blood into the body through the opening 66. As will be described below, generally the opening 62 is spaced sufficiently distant from the opening 64 so that a sufficient blood drainage can be had from both the SVC and the IVC. The third opening 66 is sufficiently spaced between the openings 62, 64 to allow blood infusion into the heart, such as the atrium 12 of the heart, described in FIG. 1.

An introducer 80 can be used to help facilitate the cannula assembly insertion through the SVC 4, through the atrium 12, and into the IVC 6 region. The introducer 80 is specifically small enough and tapered to be an atraumatic introducer.

Further, an indicator portion 102 can be coupled to the cannula assembly to assist in externally locating the assembly upon insertion. The indicator portion can be, for example, radio opaque. The indicator portion can include a discrete element attached to the cannula assembly, or a material integrally formed with the material of the cannula assembly. The indicator portion 102 can be located at any appropriate location on the cannula assembly.

Figure 2C:
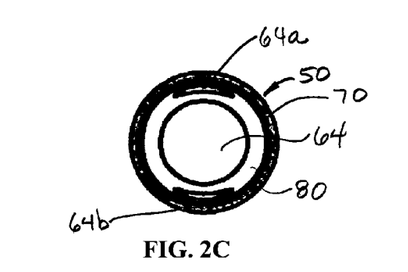
FIG. 2C is a cross-sectional view of the lower portion of the cannula assembly of FIG. 2, insertable into the IVC.

FIG. 2C is a cross-sectional view of the lower portion of the cannula assembly of FIG. 2, insertable into the IVC. The cannula assembly 50 includes a cannula assembly sidewall 70. Since the cannula assembly sidewall 70 at the location shown in FIG. 2C is transitioned into primarily one lumen, the sidewall 70 effectively becomes the sidewall of the single lumen in that location. At the particular location of the cross-section shown in FIG. 2C, the cannula assembly 50 and cannula assembly sidewall 70 show the drainage lumen 54 that extends into the IVC. The introducer 80 is shown as a tapered portion from an inside view. The openings 64, 64a, 64b are illustrated, as previously described, the one or more openings generally referred to herein as opening 64.

Figure 2D:
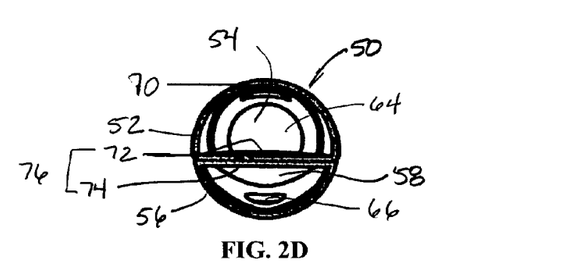
FIG. 2D is a cross-sectional schematic view of a midsection of the cannula assembly of FIG. 2.

FIG. 2D is a cross-sectional schematic view of a midsection of the cannula assembly of FIG. 2. At the particular point location of the cross-section shown in FIG. 2D, the cannula assembly 50 having a cannula assembly wall 70 illustrates the dual lumen. In this embodiment, the drainage cannula 52 with its sidewall forms a drainage lumen 54. The drainage lumen 54 ultimately ends at the opening 64. The drainage cannula 52 is coupled to the infusion cannula 56, also having a sidewall to form the infusion lumen 58. For manufacturing simplicity, the cannulae are joined at a septum 76. The septum 76 can, in one embodiment, be formed from portions of the sidewalls of each of the cannula. For example, a sidewall portion 72 of the cannula 52 can be coupled to a sidewall portion 74 of the infusion cannula 56. The term "coupled," "coupling," and like terms are used broadly herein and can include any method or device for securing, binding, bonding, fastening, attaching, joining, inserting therein, forming thereon or therein, communicating, or otherwise associating, for example, mechanically, magnetically, electrically, chemically, directly or indirectly with intermediate elements, one or more pieces of members together and can further include integrally forming one functional member with another. The coupling can occur in any direction, including rotationally.

In some embodiments, the septum can be somewhat rigid. In other embodiments, described below, the septum 76 can be flexible. Also shown, is the opening 66 formed in the infusion cannula 56 that is fluidicly separate from the opening 64.

Figures 3, 3A:
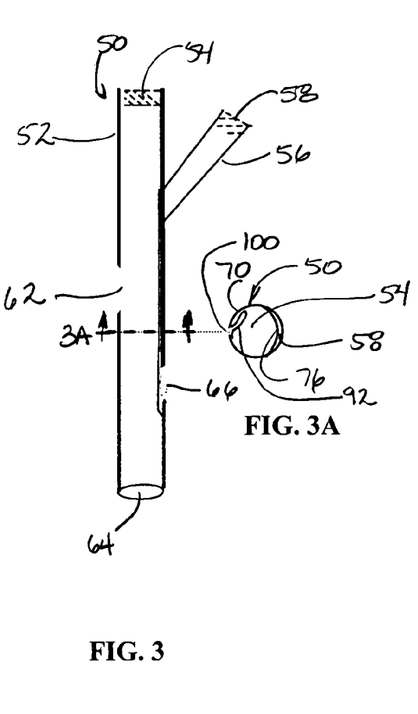
FIG. 3 is a longitudinal cross-sectional schematic diagram of one embodiment of the cannula assembly having an internal septum.
FIG. 3A is a cross-sectional schematic diagram of the cannula assembly of FIG. 3.

FIG. 3 is a longitudinal cross-sectional schematic diagram of one embodiment of the cannula assembly having an internal septum. The embodiment of FIG. 3 is related to the embodiment shown in FIGS. 2-2D. In this embodiment, the cannula assembly 50 is expandable. Thus, it can be inserted into the veins in a collapsed position to produce less trauma on the patient. Once in position, the cannula assembly 50 can be expanded in at least one lumen to facilitate the drainage and/or infusion of the blood. Advantageously, the cannula assembly can be collapsed again to facilitate removal. Similar components are similarly labeled as have been described above.

The cannula assembly 50 includes a drainage cannula 52 having a drainage lumen 54 coupled with a infusion cannula 56 having an infusion lumen 58. Openings 62, 64 are fluidicly coupled to the drainage lumen 54. For purposes of illustration, the introducer 80 is not shown, although would generally be present. A third opening 66 is fluidicly coupled to the infusion lumen 58 and separated from the openings 62, 64.

FIG. 3A is a cross-sectional schematic diagram of the cannula assembly of FIG. 3. The unexpanded cannula assembly 50 facilitates percutaneous insertion and advancement. An internal septum 76 separates the two lumen, such as the drainage lumen 54 and the infusion lumen 58. The flexible septum can be disposed adjacent a cannula assembly sidewall 70 on the infusion lumen side, so as to make the cannula assembly body effectively a single lumen for an introducer. The pressure difference (negative pressure in drainage lumen and positive pressure in infusion lumen) makes the septum flip into the drainage lumen and the infusion lumen is formatted to an enlarged cross-sectional area.

Figures 4, 4A:
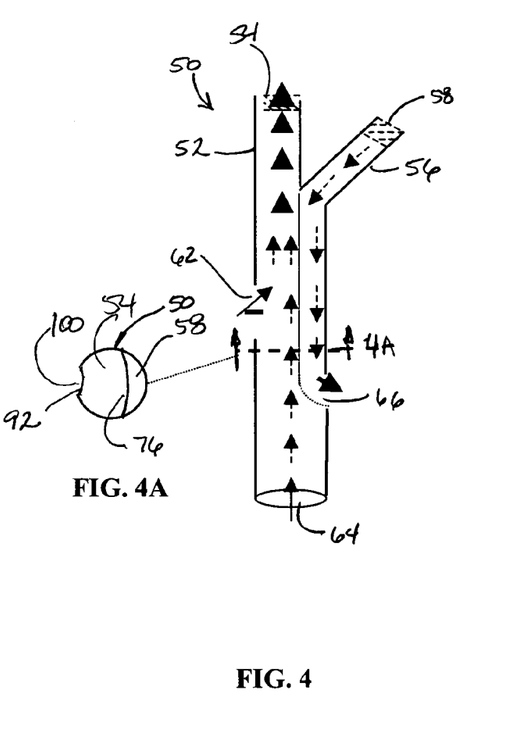
FIG. 4 is a longitudinal cross-sectional schematic diagram of the cannula assembly of FIG. 3 in an expanded state.
FIG. 4A is a cross-sectional view of the cannula assembly of FIG. 4.

FIG. 4 is a longitudinal cross-sectional schematic diagram of the cannula assembly of FIG. 3 in an expanded state. FIG. 4A is a cross-sectional view of the cannula assembly of FIG. 4. Both figures will be described in conjunction with each other. The cannula assembly 50 includes at least one expandable lumen. For illustrative purposes, the lumen shown expanded is the infusion lumen 58. The septum 76, being flexible, has flexed to allow a greater cross-sectional area for the infusion lumen 58. In at least one embodiment, the infusion lumen 58 can expand when the blood flows back through the infusion lumen with a pressure that is greater then the blood flow out of the drainage lumen 54.

Further, the overall size of the cannula assembly 50 can also expand. In at least one embodiment, the extension can occur by use of a slot 100 in the cannula assembly 50, as will be described in more detail below. In general, the slot 100 is a longitudinal slot extending at least partially down the cannula assembly. The slot 100 can be located in either the drainage lumen 54 or the infusion lumen 58. To maintain flow integrity, a flexible portions 92, described further in FIG. 12 can be used.

In general, blood flow through the drainage lumen 54 occurs from the opening 64 located below the Eustachian valve 7, described in FIG. 1. The opening 62 allows blood flow from the SVC 4 (also in FIG. 1) into the drainage lumen 54. In at least one embodiment, the blood is processed and returned to the body through the infusion cannula 58 and the opening 66 into the atrium 12 of the heart, described in FIG. 1.

Figure 5:
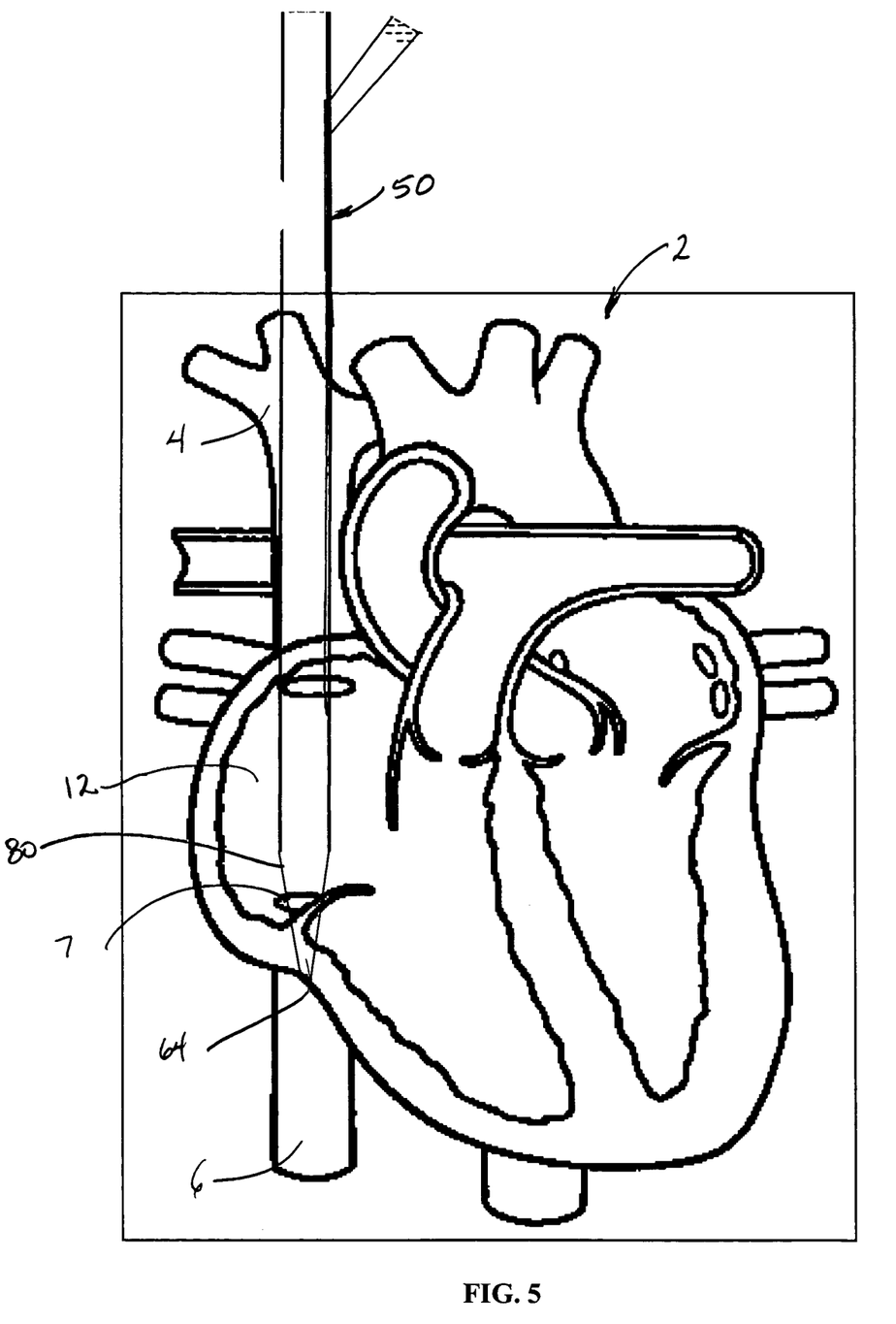
FIG. 5 is a schematic diagram of the cannula assembly of the present invention, illustrating insertion through the SVC and into the IVC of the heart with an atraumatic introducer.

FIG. 5 is a schematic diagram of the cannula assembly of the present invention, illustrating insertion through the SVC 4 and into the IVC 6 of the heart with an atraumatic introducer 80. One of the novel aspects of the present invention is the insertion of the cannula assembly 50 through both the SVC 4 and the IVC 6. Heretofore, such procedures have been traumatic and avoided. The present invention is able to accomplish both by a combination of factors, including use of an atraumatic introducer 80 described above. The cannula assembly 50 with the introducer 80 allows percutaneous insertion by a jugular vein approach, with simplified advancement through the SVC 4, the right atrium 12, into the IVC 6. Importantly, the introducer 80 helps avoid trauma to the Eustachian valve 7.

Figure 6:
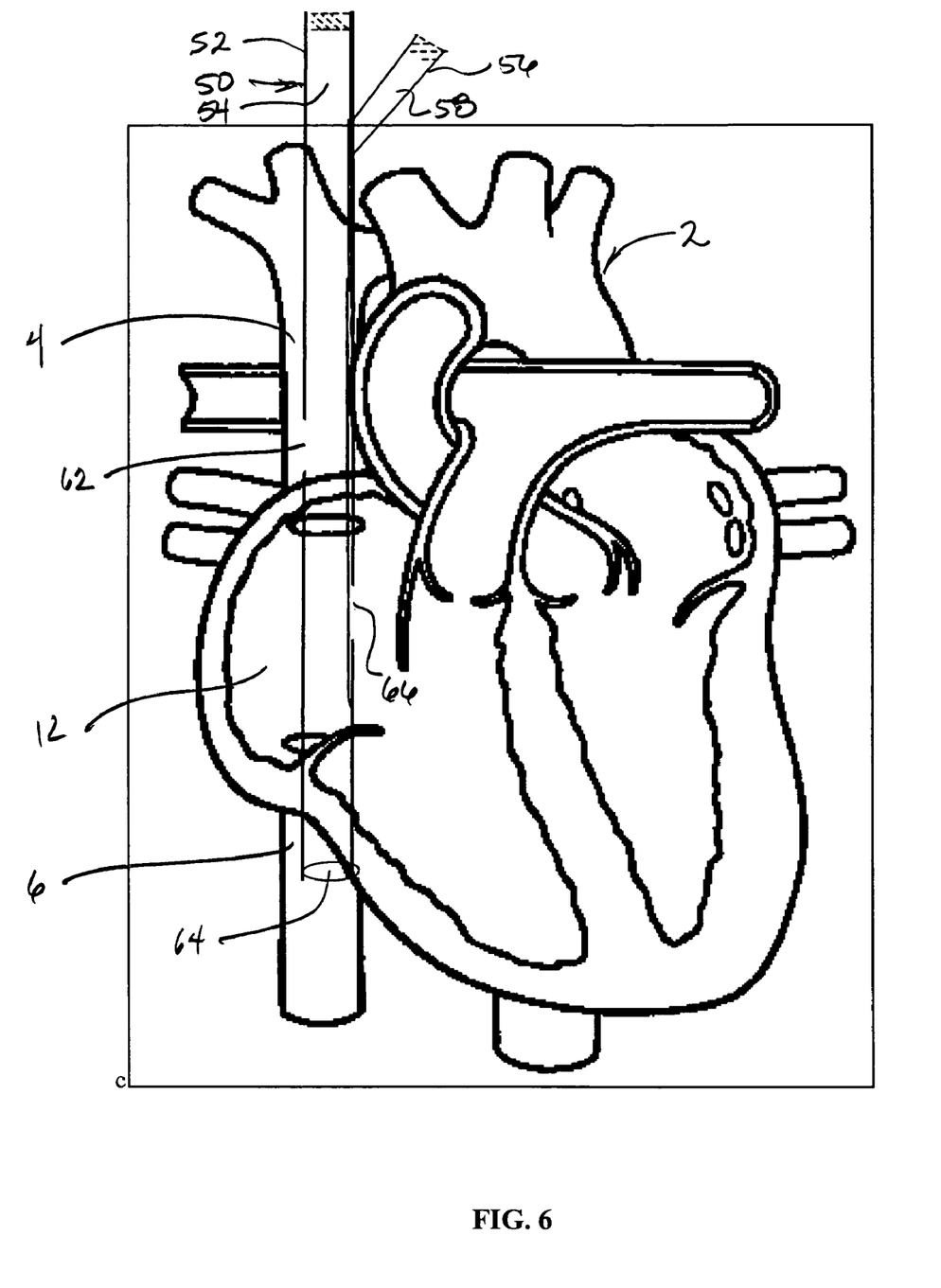
FIG. 6 is a schematic diagram of the cannula assembly and heart of FIG. 5 with the cannula assembly in position.

FIG. 6 is a schematic diagram of the cannula assembly and heart of FIG. 5 with the cannula assembly in position. A cannula assembly 50 can be placed into the heart through the jugular vein and through the SVC 4, the right atrium 12, and into the IVC 6. The opening 64 allows blood drainage from the lower part of the body through the IVC. The term IVC is broadly used herein and includes a portion of the venous system into which blood flowing from the lower part of the body is collected prior to entering the atrium 12. Similarly, the term SVC is broadly used herein and includes a portion of the venous system into which blood flowing from the upper part of the body is collected prior to entering the atrium 12.

The opening 66 allows blood to return to the heart through the atrium 12. In the embodiment shown in FIG. 6, the cannula assembly 52 appears in an unexpanded state. If, for example, the particular embodiment used is an expandable cannula assembly 50, then the cannula assembly can be expanded. It is generally considered advantageous to expand the cannula assembly to increase the cross-sectional area of the lumen to allow greater blood flow while decreasing blood trauma.

Figure 7:
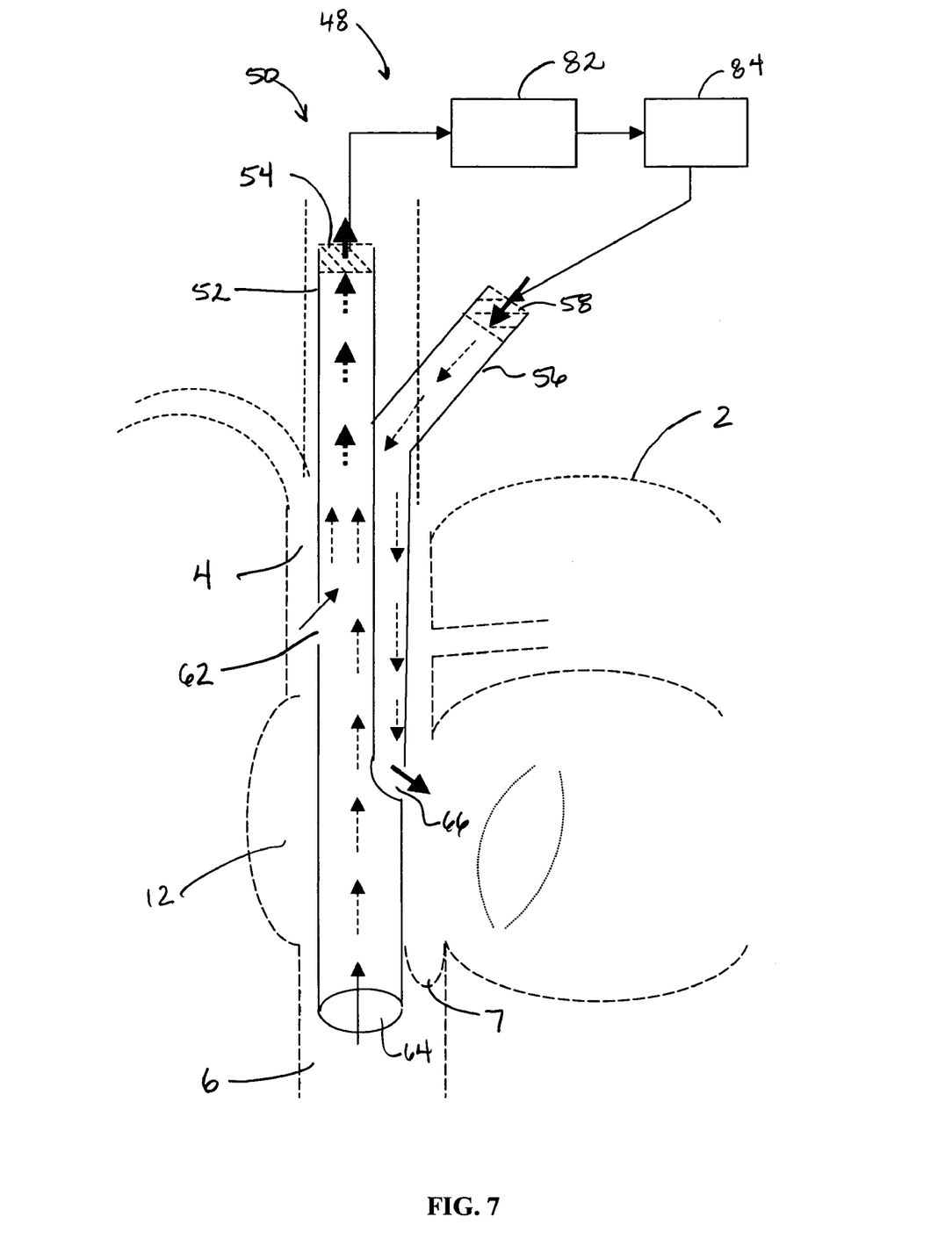
FIG. 7 is a schematic diagram of a system with the cannula assembly, illustrating flow paths for the blood.

FIG. 7 is a schematic diagram of a system with the cannula assembly, illustrating flow paths for the blood. The cannula assembly 50 can be coupled to the components that collectively form a system 48 for mixing a fluid into the bloodstream of a body. In general, the system 48 can include the cannula assembly which in at least one embodiment will include a drainage cannula and an infusion cannula, a pump 82 coupled to the cannula assembly, and a mixing unit coupled to the pump, the mixing unit being coupled to the cannula assembly 50 as well.

In general, the blood will be drained from the drainage cannula 52 through the drainage lumen 54 into the pump 82. The pump 82 will provide the blood to the mixing unit 84. The mixing unit 84 in at least one embodiment will be or can be an oxygenator to perform the extra corporeal membrane oxygenation (ECMO) described above. Such units are known to those with ordinary skill in the art. Further, the pump can be located at different points in the process or combined with the mixing unit 84, as may be appropriate. The mixing unit 84 will return blood to the body through the infusion lumen 58 of the infusion cannula 56. The blood flow will then flow out the opening 66 into the heart. In at least one embodiment, the blood flow can enter the drainage lumen 54 through the openings 62, 64, where the opening 62 can be disposed away from the infusion opening 66. Thus, undesirable recirculation of the blood from the infusion opening 66 to the openings 62, 64 can be minimized or otherwise avoided.

In at least one embodiment, the small unexpanded cannula assembly 50 (such as 16-20 Fr) with the introducer 80 allows percutaneous insertion by a jugular vein approach, with simplified advancement through the SVC 4, the right atrium 12, and into the IVC 6. The opening 66 of the infusion lumen can be situated in the right atrium and directed toward the tricuspid valve and the right ventricle and the opening 62 can be directed away from the right ventricle. As the IVC is reached, the cannula can expand and the cannula lumens will be enlarged. The enlargement can be about 150% to 200%, although other percentages can be used as appropriate. As a result, resistance decreases and the potential for blood trauma will be minimized. The cross-sectional area ratio of the drainage lumen to the infusion lumen can be generally 2:1, although other ratios can be used as appropriate.

The openings 62, 64 in the drainage cannula 52 allow for drainage. The opening 62 rests in the SVC 4 and drains blood from the upper body. The opening 64 at the cannula tip rests in the IVC 6 and drains venous blood from the lower body. If necessary, total venous blood could be withdrawn through two individual drainage lumen openings (opening 64 in IVC and side opening 62 in SVC) for extracorporeal oxygenation. The opening 66 of the infusion lumen can be situated in the right atrium and directed toward the tricuspid valve, and the right ventricle and the opening 62 can be directed away from the right ventricle. The blood drainage and delivery openings are spatially separated, reducing or preventing undesirable oxygenated blood recirculation, and allowing substantially total extracorporeal gas exchange. Total extracorporeal gas exchange is not necessary as the patient's native lung is partially functioning and by reducing or eliminating recirculation, the demand of the extracorporeal blood flow for partial extracorporeal oxygenation and potential blood trauma is generally reduced. As the result, the limit of ECMO safe duration can be extended.

The embodiments illustrated in FIGS. 8-12A are simply alternative embodiments based upon the underlying principals of the present invention. Other embodiments are possible and the invention is not limited to those shown herein.

Figure 8:
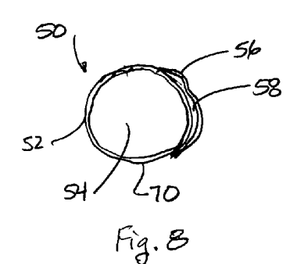
FIG. 8 is a cross-sectional schematic diagram of a cannula assembly having an external lumen.
Figure 8A:
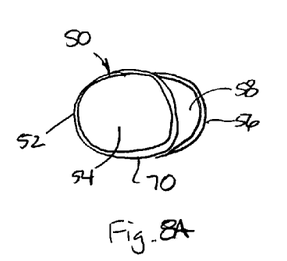
FIG. 8A is a cross-sectional schematic diagram of the cannula assembly of FIG. 8 with an expanded external lumen.

FIG. 8 is a cross-sectional schematic diagram of a cannula assembly having an external lumen. FIG. 8A is a cross-sectional schematic diagram of the cannula assembly of FIG. 8 with an expanded external lumen. The figures will be described in conjunction with each other. The cannula assembly 50 can include a lumen external to the main body. For example, the cannula assembly 50 can include the drainage cannula 52 forming a drainage lumen 54 within the cannula assembly sidewall 70. A second lumen, such as the infusion lumen 56, can be formed external to the cannula assembly sidewall 70. The sidewall of the lumen 56 can be flexible, so that in a contracted state, the cross-sectional area of the infusion lumen 58 is minimal. However, after insertion and when appropriate, the flexible sidewall of the infusion lumen 56 can expand. The expansion allows a greater cross-sectional area for the infusion lumen 58, as illustrated in FIG. 8A.

While the illustration shows a smaller cross-sectional area for the infusion lumen 58 relative to the drainage lumen 54, it is to be understood that the illustration is only schematic and the cross-sectional area can be larger, equal to or smaller then the drainage lumen 54. Further, the drainage lumen 54 can be external to the sidewall 70 of the cannula assembly 50 and the infusion lumen 58 can be internal to the sidewall 70.

Figure 9:
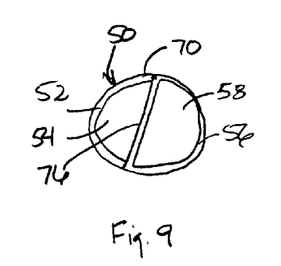
FIG. 9 is a cross-sectional schematic view of a cannula assembly with an internal septum.

FIG. 9 is a cross-sectional schematic view of a cannula assembly with an internal septum. The cannula assembly 50 can include both lumen 54, 58 within the cannula assembly sidewall 70. In essence, the septum 76 separates the sidewall 70 into two portions, a first portion, functioning as a drainage cannula 52 and a second portion functioning as an infusion cannula 56 with each respective lumen.

Figure 10:
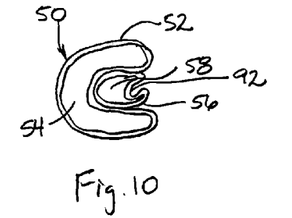
FIG. 10 is a cross-sectional schematic diagram of a cannula assembly having a non-circular shape.
Figure 10A:
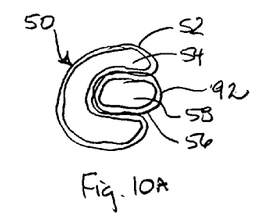
FIG. 10A is a cross-sectional schematic diagram of the cannula assembly of FIG. 10 in a different condition.

FIG. 10 is a cross-sectional schematic diagram of a cannula assembly having a non-circular shape. FIG. 10A is a cross-sectional schematic diagram of the cannula assembly of FIG. 10 in a different condition. In some embodiments, it may be advantageous to configure the cross-sectional area of the lumen 54, 58 in a noncircular fashion. While the generally understood concept is to use a circular cannula due to the circular nature of the veins or arteries into which it is inserted, the present invention can use noncircular portions of the cannula assembly 50 in various ways. For example, one of the lumens, such as lumen 54 could be shaped in a "U." The other lumen, such as the infusion lumen 58, could be coupled to the open portion of the "U." Thus, the single cannula assembly can form an overall circular shape and be inserted into the circular veins with less trauma than two side-by-side individually circular cannula.

In at least one embodiment, one or more of the lumen can include a flexible portion 92. As shown in FIG. 10A, the flexible portion 92 can expand at various points in the process, such as after positioning in the vein. The expansion can be designed to occur upon a number of actuating events, such as heat from the body, pressure from the returning blood flow through the infusion lumen, and other actuating events.

Figure 11:
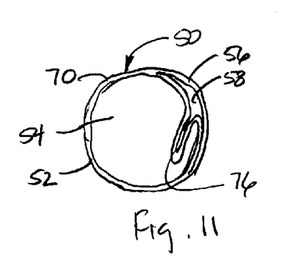
FIG. 11 is a cross-sectional schematic diagram of the cannula assembly having a flexible septum for expansion.
Figure 11A:
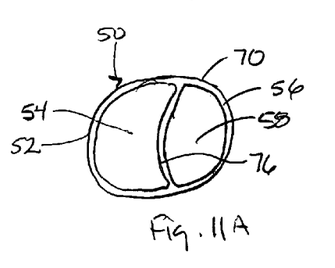
FIG. 11A is a cross-sectional schematic diagram of the cannula assembly of FIG. 11 with the septum and a lumen in an expanded condition.

FIG. 11 is a cross-sectional schematic diagram of the cannula assembly having a flexible septum for expansion. FIG. 11A is a cross-sectional schematic diagram of the cannula assembly of FIG. 11 with the septum and a lumen in an expanded condition. The cannula assembly 50 can include a septum 76 that is flexible. The flexible septum 76 fluidicly separates the drainage cannula 52 having a drainage lumen 54 from the infusion cannula 56 having an infusion lumen 58. As illustrated in FIG. 11A, the flexible septum 76 can flex into a different position to vary the cross-sectional flow area of one or both of the lumen 54, 58.

Figure 12:
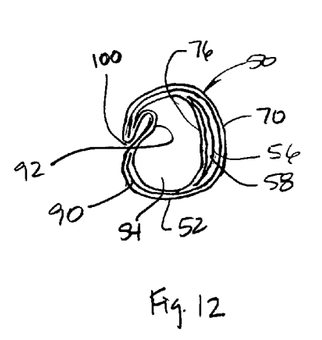
FIG. 12 is a cross-sectional schematic diagram of the cannula assembly having a flexible portion coupled to both sides of a swab in the cannula assembly and a flexible septum internal to the cannula assembly.
Figure 12A:
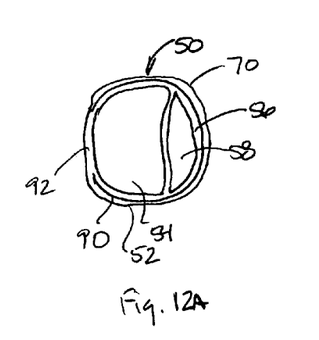
FIG. 12A is a schematic diagram of the cannula assembly of FIG. 12 in an expanded state.

FIG. 12 is a cross-sectional schematic diagram of the cannula assembly having a flexible portion coupled to both sides of a swab in the cannula assembly and a flexible septum internal to the cannula assembly. FIG. 12A is a schematic diagram of the cannula assembly of FIG. 12 in an expanded state. The figures will be described in conjunction with each other.

As described above, it can be advantageous to insert a smaller collapsed cannula assembly 50 into the SVC, atrium, and IVC, followed by an expansion of either the cannula assembly as a whole or a portion of the cannula assembly. In one particular embodiment, the cannula assembly can be expanded by an expandable element 90 within the cannula assembly. In at least one embodiment, the expandable element 90 can be formed within the cannula assembly sidewall 70. A slot 100 can be formed in the cannula assembly 50, so that the expandable element 90 forms a "C." However, because flow is generally contained within the cannula assembly 50, such as through the lumen 54, a flexible portion 92 can be coupled to both sides of the slot 100 and seal the slot 100. A flexible septum 76 can separate the lumen 54 from the lumen 58.

The expandable element 90 can be a continuous structure or a series of discrete elements, such as hoops formed longitudinally with the cannula assembly for the portion of the cannula assembly that is desired to expand. In at least one embodiment, the expandable element 90 can include a memory shape alloy, such as nickel titanium, also known as NiTi or Nitinol. Other memory shape materials would be known to those with ordinary skill in the art, given the description contained herein. Further, some materials will expand with electrical energy, generally due to the resistance of the expandable element and the heat generated thereby.

For those embodiments with the expandable element, the cannula assembly could be inserted into an appropriate position. Heat from the body can be used to actuate the expandable element, such as the memory shape alloy, and expand the cannula assembly 50 to allow greater cross-sectional area for one or more of the lumen. Alternatively, an electrical charge can be sent through the cannula assembly to expand the expandable element 90.

To collapse the cannula assembly, the electrical current can be interrupted, or the expandable element can be cooled, such as with a cooled saline solution. The cannula assembly 50 can then be withdrawn from the body.

Figure 13:
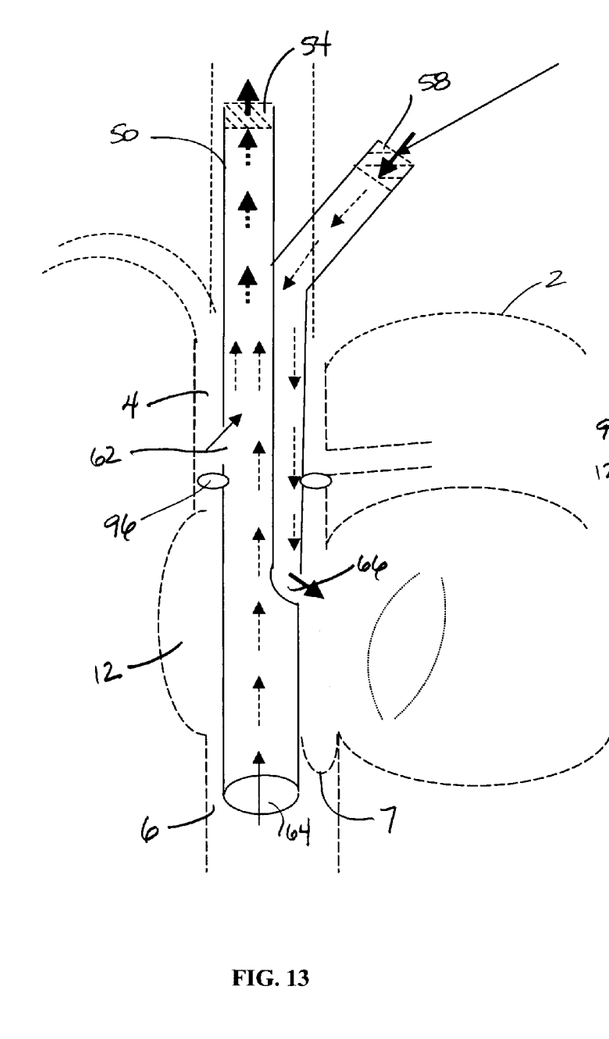
FIG. 13 is a schematic diagram of a cannula assembly in a heart having an expandable seal surrounding at least part of the cannula assembly.

FIG. 13 is a schematic diagram of a cannula assembly in a heart having an expandable seal surrounding at least part of the cannula assembly. The cannula assembly 50 provides distinct advantages over other efforts known in the field. To further enhance a cannula assembly 50 performance, an expandable seal 96 can be coupled to at least a portion of the external surface of the cannula assembly 50. In at least one embodiment, the expandable seal 96 can be located on the cannula assembly between the opening 62 of the drainage lumen 54 and the opening 66 of the infusion lumen 58. The expandable seal 96 helps reduce inadvertent and undesirable blood recirculation from the opening 66 of oxygenated blood to the opening 62 of deoxygenated blood. The Eustachian valve 7 helps resist undesirable recirculation between the opening 64 and the opening 66.

The expandable seal can include an inflatable balloon seal, memory shape alloy seal, and other expandable and generally contractable seals. In at least one embodiment, the expandable seal can be concentrically disposed around at least a portion of the cannula assembly 50.

Further, the expandable seal 96 can place a distance between the sidewall of the SVC and the opening 62 to avoid an undesirable collapse of the SVC sidewall against the opening 62 that restricts blood flow. Thus, the expandable seal 96 can both reduce recirculation from the opening 66 to the opening 62 and allow increased blood flow into the opening 62 from the SVC 4.

Figure 13A:
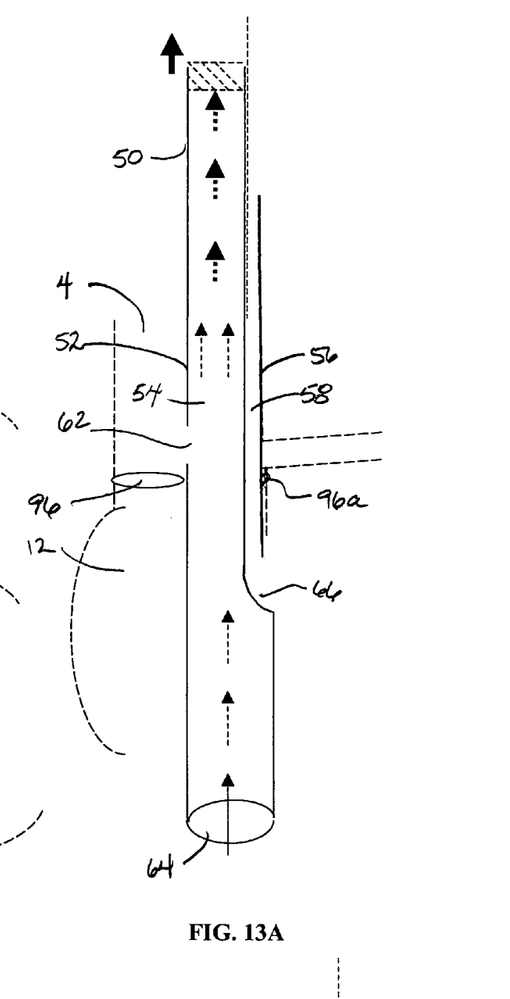
FIG. 13A is a schematic diagram of a cannula assembly in a heart with an eccentric expandable seal surrounding at least part of the cannula assembly.

FIG. 13A is a schematic diagram of a cannula assembly in a heart with an eccentric expandable seal surrounding at least part of the cannula assembly. Similar to the embodiment shown above in FIG. 13, an expandable 96 can be disposed at least partially around the cannula assembly 50. In some embodiments, it can be advantageous to eccentrically dispose the expandable seal 96 around the cannula assembly 50. For example, at some volumetric rates of blood flow, the sidewall of the SVC 4 can collapse against the opening 62 and restrict blood flow into the opening 62. An eccentric expandable seal 96 can increase the distance between the opening 62 and the SVC sidewall.

Figure 14:
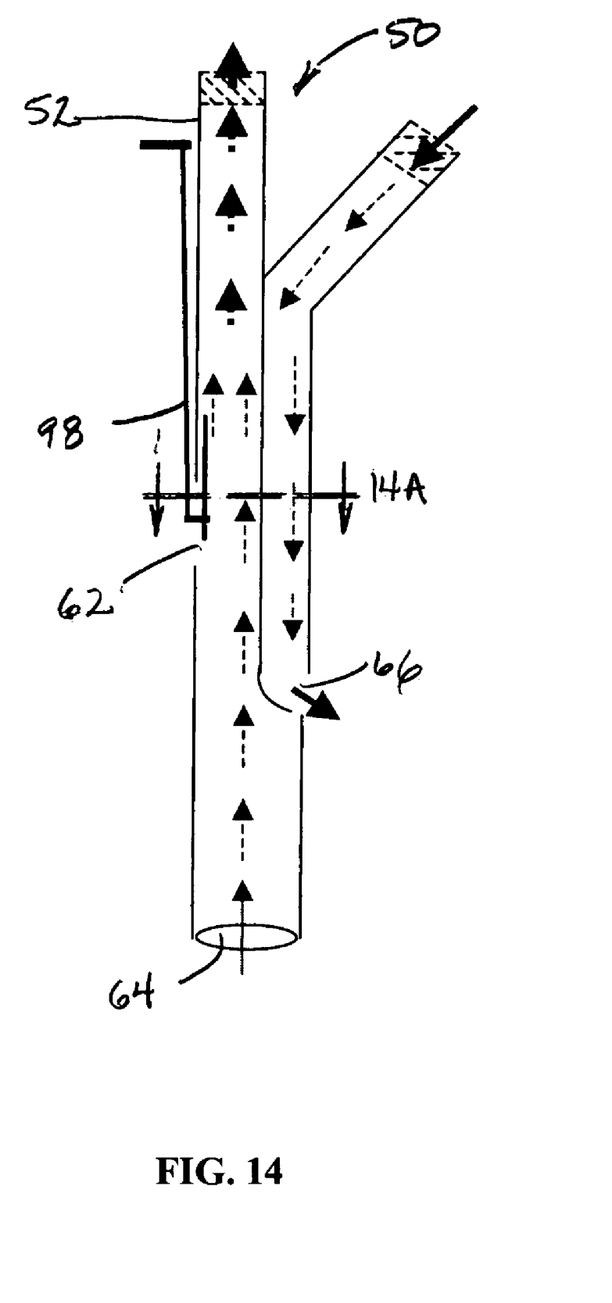
FIG. 14 is a longitudinal cross-sectional schematic diagram of another embodiment of the present invention having an adjustable flow controller.
Figure 14A:
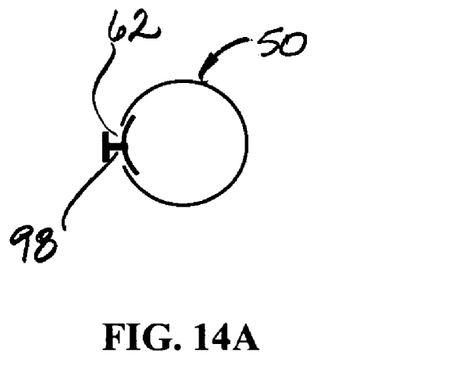
FIG. 14A is a cross-sectional schematic diagram through the cannula assembly of FIG. 14.

FIG. 14 is a longitudinal cross-sectional schematic diagram of another embodiment of the present invention having an adjustable flow controller. FIG. 14A is a cross-sectional schematic diagram through the cannula assembly of FIG. 14. This embodiment includes a flow controller 98 disposed in at least one of the openings 62, 64, 66. Generally, it is envisioned that the flow controller 98 can be disposed in the opening 62 to adjust the relative flows into the drainage cannula 52. In at least one embodiment, the flow controller 98 can be an adjustable slide that selectively covers some percentage from 0-100% of the opening 62. Thus, for some applications, it may be desirable to balance the flows between the opening 62 and 64, so that an equal portion of blood is obtained from the upper body and the lower body of the patient. In other scenarios, it may be advantageous to obtain a greater portion from the lower body having a greater percentage of the blood in the body. The flow controller 98 can allow for such variations.

The blood resistance from the IVC and the SVC can be adjusted by sliding the occlusion device incorporated into the opening 62. Further, this procedure allows blood to be withdrawn from both locations proportional to a return flow despite minor fluctuations in a supply rate.

Table 1 briefly highlights various attributes of the present invention compared to other known technologies, where the following abbreviations are used:

ECMO: Extracorporeal Membrane Oxygenation
DLVV: Double Lumen Veno-venous
VV: Veno-veous
VVV: 2 drain veno-1 infuse venous

TABLE 1

Comparison of Four Existing VV ECMO with New Technology

| Parameter | Two site VV ECMO | DLVV ECMO | Tidal Flow VV ECMO | VVV (three site) ECMO | PRESENT INVENTION (in at least one embodiment) |
|---|---|---|---|---|---|
| Cannula type and Number | 2 Single lumen | 1 Double lumen | 1 Single lumen | 3 Single lumen | 1 Double lumen |
| Multiple cannulation | Yes | No | No | Yes | No |
| Cannulation site | Jugular v (Drain) Femoral V (Infuse) | Jugular V | Jugular V | Jugular V (drain) Iliac V (drain) IVC (infuse) | Jugular V |
| Circuit | Long and complicated | Simple | Long and Very complicated | Very long and very complicated | Short and simple |
| Recirculation | Yes | Yes | Yes | No | No |
| Venous drainage | Insufficient | Insufficient | Insufficient | Near total | Near total |
| Gas Exchange | Insufficient | Insufficient | Insufficient | Near total | Near total |
| Blood Flow demand for enough gas exchange | High | High | High | Low | Low |
| Blood trauma | High | High | High | High | Low |

In summary, the VV ECMO system described here can be performed with one or more of the following benefits:
1. Avoid blood recirculation and decrease the demand for extracorporeal blood flow for gas exchange;
2. Capability to achieve substantially total venous blood drainage for total extracorporeal oxygenation;
3. Avoid multiple cannulations;
4. Minimally invasive, single percutaneous cannulation;
5. Simple circuit and effective system;
6. Less blood trauma.

EXAMPLE 1

The example demonstrates the ability to receive relatively high flow rates of blood through both the IVC and SVC with minimal recirculation from the infusion cannula. A 38-kilogram sheep having a similar size heart, SVC, and IVC as a medium-sized human was heavily sedated, so that the sheep was not breathing, requiring total dependence upon the blood flow and oxygenation of the system. The drainage cannula was inserted through the jugular vein and placed into position to the SVC for drainage therefrom. The cannula was extended through the atrium, through the Eustachian valve, and into the IVC for drainage from the IVC as well. An infusion cannula was likewise inserted into the right atrium. Blood sampling points included the IVC, the SVC, a pre-oxygenation sampling of combined SVC and IVC blood, a post-oxygenation sampling after the oxygenator, and a control sampling point in a carotid artery.

Normal blood flow for a sheep of this size is about three liters per minute. Prior efforts indicated that a maximum of about 30% from the SVC would be expected, that is about 1 liter per minute. In contrast, the present invention was able to flow approximately 80% from both the SVC and IVC, that is, about 2.5 liters per minute. The increased blood flow obtained from the present system was a remarkable increase using only one cannula to drain both the IVC and SVC venous blood.

The quality of the blood flow was then examined. Table 2 illustrates the results of the various sampling of the five sampling points.

TABLE 2

Oxygenation Results of ECMO

| Sampling Point | Characteristic | Result |
| --- | --- | --- |
| IVC (prior to entrance to drainage cannula) | $PCO_2$ | 46.5 |
| | $PO_2$ | 25 |
| | $O_2S$ | 21.4 |
| SVC (prior to entrance to drainage cannula) | $PCO_2$ | 42.1 |
| | $PO_2$ | 40 |
| | $O_2S$ | 49.7 |
| Artery | $PCO_2$ | 30.6 |
| | $PO_2$ | 94 |
| | $O_2S$ | 92.9 |
| Pre-Oxgenation (post entrance to drainage cannula) | $PCO_2$ | 36.5 |
| | $PO_2$ | 42 |
| | $O_2S$ | 8.2 |
| Post-Oxgenation (prior to infusion into body) | $PCO_2$ | 25.3 |
| | $PO_2$ | 485 |
| | $O_2S$ | 95.9 |

The value of $PCO_2$, expressed in mmHg, is the partial pressure of carbon dioxide that is dissolved in the blood. $PO_2$, also expressed in mmHg, is the partial pressure of oxygen that is dissolved in the blood plasma, not the amount held in the red blood cells bound to hemoglobin. The value of $O_2S$, expressed as a percentage, stands for oxygen saturation, which is the total amount of oxygen bound to hemoglobin in the red blood cells in comparison to the total amount possible. For example, if the $O_2S$ is 50%, the hemoglobin is carrying only half of what it is capable of carrying. For the purposes of the example, the SVC $PO_2$ and pre-oxygenation $PO_2$ were substantially identical. Because the SVC blood $PO_2$ upstream of the cannula assembly was substantially identical to the $PO_2$ value of the blood within the cannula assembly, the close values indicate that little or no recirculation from the returning infusion cannula occurred.

Noticeably, this example did not include the use of the expandable seal 96 described in reference to FIG. 13. It is possible that at higher flow rates, the advantages of the expandable seal 96 might be noticed.

The data also shows that the post-oxygenation blood had an oxygen saturation $O_2S$ value of 96%. The sample in the carotid artery had an $O_2S$ value of 93%. Such high figures, indicate that even with the animal so heavily sedated that it was not breathing, the animal would readily survive due to the highly efficient oxygenation of the majority of its blood flow.

The present invention provides a less traumatic system, method, and device for draining significantly large volumes of blood and mixing a fluid, such as oxygen, into the blood, and returning the blood to the body, such as in the atrium of the heart, while substantially reducing undesirable recirculation between the drainage opening and the infusion opening.

Various basics of the invention have been explained herein. The various techniques and devices disclosed represent a portion of that which those skilled in the art would readily understand from the teachings of this application. Details for the implementation thereof can be added by those with ordinary skill in the art. The accompanying figures may contain additional information not specifically discussed in the text and such information may be described in a later application without adding new subject matter. Additionally, various combinations and permutations of all elements or applications can be created and presented. All can be done to optimize performance in a specific application.

The various steps described herein can be combined with other steps, can occur in a variety of sequences unless otherwise specifically limited, various steps can be interlineated with the stated steps, and the stated steps can be split into multiple steps. Unless the context requires otherwise, the word "comprise" or variations such as "comprises" or "comprising" or the word "includes" and variations, should be understood to imply the inclusion of at least the stated element or step or group of elements or steps or equivalents thereof, and not the exclusion of any other element or step or group of elements or steps or equivalents thereof.

Further, any documents to which reference is made in the application for this patent as well as all references listed in any list of references filed with the application are hereby incorporated by reference. However, to the extent statements might be considered inconsistent with the patenting of this invention such statements are expressly not to be considered as made by the applicant(s).

Also, any directions such as "top," "bottom," "left," "right," "upper," "lower," and other directions and orientations are described herein for clarity in reference to the figures and are not to be limiting of the actual device or system or use of the device or system. The device or system may be used in a number of directions and orientations.

The invention claimed is:

1. A system for mixing a fluid into a bloodstream of a body, comprising:
   a. a drainage cannula adapted to be inserted through both a superior vena cava of a heart of the body and an inferior vena cava of the heart, the drainage cannula having a first opening to receive blood from a superior vena cava blood flow and a second opening to receive blood from an inferior vena cava blood flow;
   b. an infusion cannula adapted to be inserted into the bloodstream downstream of both the superior vena cava and inferior vena cava; the drainage cannula and the infusion cannula being coupled as a single cannula assembly with at least two lumen, one lumen being the drainage cannula and the other lumen being the infusion cannula;
   c. a septum coupled between the lumen to fluidicly separate the lumen along at least a portion of a length of each lumen and adapted to flex between the two lumen to vary a cross-sectional flow area of at least one of the lumen;
   d. a pump coupled to the drainage cannula and the infusion cannula;
   e. a mixing unit coupled to the pump and adapted to mix the fluid into the bloodstream of the body; and
   f. an atraumatic introducer coupled to the cannula assembly and sized larger than a cross-sectional dimension of at least one of the lumen and adapted to pass through such lumen and cause the septum to flex toward another lumen to allow passage of the introducer.

2. The system of claim 1, further comprising an opening formed in the infusion cannula spaced along a length of the cannula assembly between the first opening and the second opening of the drainage cannula.

3. The system of claim 1, wherein the infusion cannula is adapted to infuse the fluid into an atrium of the heart through an opening in the infusion cannula.

4. The system of claim 3, wherein the opening in the drainage cannula for the superior vena cava is oriented rotationally unaligned with the opening in the infusion cannula.

5. The system of claim 1, wherein at least one of the lumen is expandable in cross-sectional flow area.

6. The system of claim 5, wherein the expandable lumen comprises a heat-sensitive expandable element adapted to change shape in use inside the body due to exposure to a different temperature inside the body than when not in use.

7. The system of claim 6, wherein the heat-sensitive expandable element comprises a memory shape alloy.

8. The system of claim 5, wherein the expandable lumen comprises an expandable sidewall and wherein the sidewall comprises a flexible portion that is adapted to sealingly expand to maintain a flow within the lumen.

9. The system of claim 8, wherein the sidewall comprises a split sidewall having a slot.

10. The system of claim 1, wherein at least one lumen is expandable in cross-sectional area.

11. The system of claim 1, wherein the single cannula sidewall is expandable and wherein the sidewall comprises a flexible portion that is adapted to sealingly expand.

12. The system of claim 1, wherein one lumen is formed inside the single cannula assembly and the other lumen is formed outside a sidewall of the single cannula assembly.

13. The system of claim 12, wherein the lumen formed outside the sidewall is expandable in cross-sectional area.

14. The system of claim 1, wherein at least one of the lumen comprises a non-circular cross-sectional shape.

15. The system of claim 1, further comprising an expandable seal disposed external to at least one of the lumen.

16. The system of claim 15, wherein the expandable seal is eccentrically disposed at least partially around at least one of the lumen and adapted to seal the lumen in an eccentric position inside a vessel in which the cannula assembly is deployed.

17. The system of claim 15, wherein the expandable seal comprises an inflatable balloon.

18. The system of claim 1, wherein a relative percentage of volumetric flow between the superior vena cava blood flow and the inferior vena cava blood flow is adjustable.

19. The system of claim 1, wherein the fluid comprises a liquid having one or more perfused gases.

20. The system of claim 1, wherein the mixing unit comprises an oxygenator and the fluid comprises oxygenated blood for veno-venous extracorporeal membrane oxygenation (VV ECMO).

21. The system of claim 1, further comprising a radio opaque portion coupled to the cannula assembly.

22. A system for mixing a fluid into a bloodstream of a body, comprising:
   a. a drainage means for discharging blood from both a superior vena cava of a heart of the body and an inferior vena cava of the heart;
   b. an infusion means for infusing the fluid into the bloodstream downstream of both the superior vena cava and inferior vena cava, the drainage means and the infusion means being coupled to form a single assembly with at least two lumen, the drainage means comprising a first lumen and the infusion means comprising a second lumen;
   c. a septum coupled between the lumen to fluidicly separate the lumen along at least a portion of a length of each lumen and adapted to flex between the two lumen to vary a cross-sectional flow area of at least one of the lumen;
   d. a pump coupled to the drainage means and the infusion means;
   e. a mixing unit coupled to the pump and adapted to mix the fluid into the bloodstream of the body; and
   f. an atraumatic introducer coupled to the assembly of the drainage means and the infusion means and sized larger than a cross-sectional dimension of at least one of the lumen and adapted to pass through such lumen and cause the septum to flex toward another lumen to allow passage of the introducer.

23. The system of claim 22, further comprising a first opening and a second opening formed in the drainage means and a third opening formed in the infusion means spaced along a length of the assembly between the first opening and the second opening of the drainage means.

24. The system of claim 22, wherein at least one of the drainage or infusion means is expandable in cross-sectional area.

25. The system of claim 24, wherein the expandable means comprises an inside expandable lumen.

26. The system of claim 24, wherein the expandable means comprises an outside expandable lumen.

27. The system of claim 22, wherein at least one of the drainage or infusion means comprises a split sidewall.

28. The system of claim 27, wherein the sidewall comprises a sealing flexible portion.

29. The system of claim 22, further comprising an expandable seal disposed external to at least one of the drainage or infusion means.

30. The system of claim 29, wherein the expandable seal is eccentrically disposed at least partially around at least one of the drainage or infusion means and adapted to seal the means in an eccentric position inside a vessel in which the assembly is deployed.

31. The system of claim 22, wherein a relative percentage of volumetric flow between the superior vena cava blood flow and the inferior vena cava blood flow is adjustable.

32. The system of claim 22, wherein the mixing unit comprises an oxygenator and the fluid comprises oxygenated blood for VV ECMO.

33. A method of perfusing a fluid into a bloodstream of a body, comprising:
   a. introducing an atraumatic introducer into a bloodstream of the body, the introducer being coupled to a single cannula assembly having a drainage cannula forming a first lumen and an infusion cannula forming a second lumen, and the first and second lumen being fluidicly separated by a septum coupled between the lumen along at least a portion of a length of each lumen and adapted to flex between the two lumen to vary a cross-sectional flow area of at least one of the lumen, the introducer being sized larger than a cross-sectional dimension of at least one of the lumen and adapted to pass through such lumen and cause the septum to flex toward another lumen to allow passage of the introducer;
   b. discharging blood through the common drainage cannula from a superior vena cava of a heart of the body and an inferior vena cava of the heart;
   c. pumping the blood through a mixing unit to combine a fluid with the blood; and d. infusing the fluid with the blood into the body through the infusion cannula.

34. The method of claim 33, wherein infusing the fluid comprises infusing the fluid into an atrium of the body.

35. The method of claim 34, further comprising positioning the cannula assembly in the body to allow the first lumen to drain blood from both vena cava and the second lumen to infuse the blood into the atrium concurrently.

36. The method of claim 33, wherein positioning the cannula assembly comprises inserting in a first diameter condition and expanding at least one of the lumen after insertion.

37. The method of claim 36, wherein expanding at least one of the lumen comprises pressurizing the lumen through an infusion flow.

38. The method of claim 37, wherein expanding at least one of the lumen comprises expanding the lumen outside a sidewall of the cannula assembly.

39. The method of claim 37, wherein expanding at least one of the lumen comprises expanding the lumen inside a sidewall of the cannula assembly.

40. The method of claim 33, further comprising sealing an external portion of at least one of the lumen against a vessel wall.

41. The method of claim 40, wherein sealing the external portion comprises sealing downstream of the drainage from the superior vena cava and upstream from the infusion of the blood into the body.

42. The method of claim 40, wherein sealing the external portion comprises sealing at least one of the lumen in an eccentric position in the vessel in which the cannula assembly is deployed.

43. The method of claim 42, wherein sealing at least one of the lumen in the eccentric position in the vessel in which the cannula assembly is deployed comprises sealing the lumen toward a vessel wall rotationally distal from an opening into the drainage cannula.

44. The method of claim 33, further comprising orienting an opening for the drainage cannula rotationally unaligned with an opening for the infusion cannula.

45. A system for mixing a fluid into a bloodstream of a body, comprising:
   a. a drainage cannula adapted to be inserted through both a superior vena cava of a heart of the body and an inferior vena cava of the heart, the drainage cannula having a first opening to receive blood from a superior vena cava blood flow and a second opening to receive blood from an inferior vena cava blood flow;
   b. an infusion cannula adapted to be inserted into the bloodstream downstream of both the superior vena cava and inferior vena cava; the drainage cannula and the infusion cannula being coupled as a single cannula assembly with at least two lumen, one lumen being the drainage cannula and the other lumen being the infusion cannula;
   c. a septum coupled between the lumen to fluidicly separate the lumen along at least a portion of a length of each lumen and adapted to flex between the two lumen to vary a cross-sectional flow area of at least one of the lumen; and
   d. an atraumatic introducer coupled to the cannula assembly and sized larger than a cross-sectional dimension of at least one of the lumen and adapted to pass through such lumen and cause the septum to flex toward another lumen to allow passage of the introducer.

46. The system of claim 45, wherein the first opening for the superior vena cava is oriented rotationally unaligned with an opening in the infusion cannula.

47. The cannula assembly of claim 45, wherein the cannula assembly is expandable in cross-sectional area and further comprising a longitudinal slot formed in a sidewall of the cannula assembly, the slot having a first side and a second side and a flexible portion sealingly coupled to the cannula assembly on both sides of the longitudinal slot to cover the slot when the cannula assembly is expanded.

48. A system for mixing a fluid into a bloodstream of a body, comprising:
   a. a drainage cannula adapted to be inserted through both a superior vena cava of a heart of the body and an inferior vena cava of the heart, the drainage cannula having a first opening to receive blood from a superior vena cava blood flow and a second opening to receive blood from an inferior vena cava blood flow;
   b. an infusion cannula adapted to be inserted into the bloodstream downstream of both the superior vena cava and inferior vena cava; the drainage cannula and the infusion cannula being coupled as a single cannula assembly with at least two lumen, one lumen being the drainage cannula and the other lumen being the infusion cannula;
   c. a septum coupled between the lumen to fluidicly separate the lumen along at least a portion of a length of each lumen and adapted to flex upon insertion of an introducer into one of the lumen;
   d. a pump coupled to the drainage cannula and the infusion cannula;
   e. a mixing unit coupled to the pump and adapted to mix the fluid into the bloodstream of the body; and
   f. an atraumatic introducer coupled to the cannula assembly and sized larger than a cross section dimension of at least one of the lumen and adapted to pass through such lumen and cause the septum to flex toward another lumen to allow passage of the introducer.

49. The system of claim 48, further comprising an expandable seal disposed external to at least one of the lumen, wherein the expandable seal is eccentrically disposed at least partially around at least one of the lumen and adapted to seal the lumen in an eccentric position inside a vessel in which the cannula assembly is deployed.

* * * * *